United States Patent [19]

Le Van Mao et al.

[11] Patent Number: 4,847,223
[45] Date of Patent: Jul. 11, 1989

[54] SUPERACIDIC CATALYSTS FOR LOW TEMPERATURE CONVERSION OF AQUEOUS ETHANOL TO ETHYLENE

[75] Inventors: Raymond Le Van Mao; Thanh M. Nguyen, both of Montreal, Canada

[73] Assignee: Concordia University, Montreal, Canada

[21] Appl. No.: 179,547

[22] Filed: Apr. 8, 1988

[51] Int. Cl.$^4$ .............................................. B01J 29/06
[52] U.S. Cl. ..................................................... 502/62
[58] Field of Search .............................. 502/62, 68, 71

[56] References Cited

U.S. PATENT DOCUMENTS 4,330,434 5/1982 Hughes .................................. 502/62
4,423,273 12/1983 Hoelderich et al. ................ 585/640
4,540,841 9/1985 Miale et al. .......................... 585/640
4,615,995 7/1986 Le Van Mao ........................ 502/64
4,698,542 6/1987 Le Van Mao et al. .............. 585/640

FOREIGN PATENT DOCUMENTS 137435 7/1985 Japan ...................................... 502/62

OTHER PUBLICATIONS

Applied Catalysis, 34, (1987), 163–179.

Primary Examiner—Carl F. Dees
Attorney, Agent, or Firm—Cushman, Darby & Cushman

[57] ABSTRACT

There is provided a catalyst comprising from 0.5 to 7% by weight of trifluoromethanesulfonic acid incorporated onto an acid-form pentasil zeolite having a Si/Al atomic ratio ranging from 5 to 50 and a process for producing same. Also within the scope of the present invention is a process for the conversion of dilute aqueous ethanol to ethylene comprising: flowing said ethanol through a catalyst comprising from 0.5 to 7% by weight of trifluoromethanesulfonic acid incorporated onto an acid-form pentasil zeolite having a Si/Al atomic ratio range from 5 to 50 at a temperature ranging from 170° to 225° C. and recovering the desired product.

6 Claims, No Drawings

SUPERACIDIC CATALYSTS FOR LOW TEMPERATURE CONVERSION OF AQUEOUS ETHANOL TO ETHYLENE

FIELD OF THE INVENTION

The present invention relates to a novel catalyst for the selective conversion of very dilute aqueous ethanol into ethylene. More particularly, the present invention relates to a ZSM-5 zeolite (acid form) onto which triflic acid (trifluoromethanesulfonic acid, $CF_3SO_3H$) has been incorporated, and to a process using this catalyst in the production of ethylene.

BACKGROUND OF THE INVENTION

The silica-rich ZSM-5 zeolite and its homologue, the ZSM-11 zeolite, belong to the crystalline alumino-silicate pentasil family. These zeolites are used in many catalytic reactions of industrial interest such as xylene isomerization, toluene disproportionation, benzene and toluene ethylation, and methanol-to-gasoline conversion among others. Their peculiar catalytic properties are mainly due to their regular framework with a pore size which is intermediate to the large pore sized zeolites (for instance, zeolites X and Y) and the small pore sized zeolites (for instance the A zeolites). The shape selectivity of the pentasil zeolites is the catalytic expression of many factors such as:

(a) the sieving effect, i.e. the capability of the zeolite to admit its pores or to reject reactive molecules having a critical diameter falling within a well defined range;

(b) the (reverse) sieving effect, i.e. the capability of the zeolite to allow product molecules having a certain critical diameter to diffuse out of its pores. Thus, in the case of a product molecule having a diameter exceeding the pore size of the zeolite, this molecule will have to undergo additional cracking into a smaller molecule before diffusing out of the zeolite;

(c) the effect on the reaction intermediates, i.e. the capability of certain active sites to determine the length and geometry of reaction intermediate species.

In the dehydration-cracking of methanol, this third factor is enhanced by using a ZSM-5 zeolite in acid or H-form i.e. one in which nearly all the sodium ions originally present in the zeolite as synthesized, have been exchanged for protons. Thus, according to the scientific literature, the (H-form) ZSM-5 zeolites, when reacted with light alcohols, including particularly methanol and ethanol, give very similar product distributions. These results are in perfect agreement with theoretical studies on the reaction mechanism, which have identified an identical first reaction step leading to olefinic precursors, namely propylene and ethylene.

The acid sites in ZSM-5 zeolites are mainly located at the zeolite channel intersectons and are also responsible for the formation of aromatics in the final products of methanol conversion. Although the "narrowness" of the zeoite channels restricts, as mentioned before, the size of reaction products to those having no more than 11 C-atoms, the acidity of the reactive sites promotes the formation of hydrocarbons having at least 4 carbon atoms from light olefinic precursors such as ethylene and propylene. Therefore, a modification of the acid sites of the ZSM-5 zeolites is warranted if the production of shorter hydrocarbons such as ethylene is desired. By activating the zeolite at high temperature, Lewis acid sites are also formed by dehydroxylation of the zeolite surface.

In any event, it is now also through that the acid character of the acid form of the ZSM-5 zeolites originates in the Bronsted centres created by the tetrahedral aluminium sites.

According to the actual prior art, ethanol conversion over gamma-alumina mostly leads to the corresponding ether and only a small amount of ethylene is normally formed. Higher selectivities to ethylene may be obtained with very acidic aluminas and under certain reaction conditions.

Ethanol reacts over certain oxides such as thorium, chromium or titanium oxides to produce simultaneously ethylene and acetaldehyde, a dehydrogenation product. The decomposition of ethanol over supported thoria catalysts produces almost exclusively ethylene. However, conversion rates are low and an ethanol concentration of at least 90% is necessary to provide a significant yield in ethylene. In fact, if the dehydration of alcohol is performed over the afore mentioned thorium, chromium or titanium oxide catalysts with ethanol in very dilute aqueous solutions (2 to 19 vol % of ethanol in water), the yield in ethylene is low although the selectivity to ethylene in the product hydrocarbons can be very high. This is due to the fierce competition in the absorption onto the catalyst surface, between the molecules of ethanol and water. The detrimental effect of water on the yield in ethylene is due to the stronger adsorption of water on the hydrophilic active sites of the catalyst.

The silica-rich ZSM-5 zeolites, on the other hand, exhibit a large hydrophobic surface which prevents saturation of the catalyst surface by water molecules.

In 1984, a study done by G.A. Aldridge et al. and published in Ind. Eng. Chem. Process Res. Dev. 23, 733–737 (1984) showed that the catalytic conversion of ethanol from fermentation broths to gasoline over a pentasil type zeolite was at the time the most efficient in terms of energy requirement. Such a process comprises two steps:

(a) distillation of the fermentation broth in order to obtain a 60 wt% ethanol aqueous solution (as optimum concentration of ethanol, suitable for the next catalytic step) and then;

(b) catalytic reaction at 300° C. after a compression of the resulting vapors up to 8 atm.

Of course, the major inconvenient of such a technique is the need to perform distillation of dilute ethanol solutions in order to obtain significant yields in the conversion of ethanol to ethylene.

This problem has been overcome in U.S. Pat. No. 4,698,452 which discloses a process for producing light olefins and ethylene in very high yields. This process comprises flowing an aqueous ethanol solution having an ethanol concentration ranging from 2 to 10% by volume through a modified pentasil-type zeolite catalyst at a temperature ranging from 300° to 450° C. The modified catalyst used in U.S. Pat. No. 4,698,452 is a pentasil-type zeolite in which Zn and Mn have been incorporated.

However, the process described in U.S. Pat. No. 4,698,452 is still quite expensive commercially because even though the distillation step has been eliminated, the conversion reaction still has to be performed at a temperature of at least 300° C.

The reaction temperature problem has been partially overcome in U.S. application Ser. No. 102,474 filed Sept. 29, 1987 in the names of R. Le Van Mao and L.H. Dao. This application discloses the use of a steam-treated ZSM-5 zeolite in the production of ethylene from ethanol in water at very low concentrations.

However, as it was the case for the Zn/Mn bearing zeolites of U.S. Pat. No. 4,698,452, the steam-treated ZSM-5 zeolites of U.S. Ser. No. 102,474 again need relatively high temperatures (higher than 275° C.) to completely convert a 2 to 19% aqueous ethanol solution into ethylene. In both cases, such severe reaction temperatures apart from being relatively expensive in terms of large scale commercial operations, favors the thermal decomposition of the leftover glucose and other fermentation residues in the untreated ethanol fermentation broth. The resulting carbon species block the active centers of the catalyst and thereby considerably shorten is active life.

Therefore, a catalyst that could convert very dilute aqueous ethanol solutions to ethylene at low temperatures, thereby preventing thermal conversion of glucose and other fermentation residues and lowering the costs of commercial exploitation associated with high temperatures would be highly desirable.

SUMMARY OF THE INVENTION

In accordance with the present invention, there is provided a catalyst useful in the low temperature conversion of dilute ethanol solutions into ethylene.

Also within the scope of the present invention is a process for the production of such a catalyst. This process comprises incorporation triflic acid (trifluoromethanesulfonic acid, $CF_3SO_3H$) onto an acid-form ZSM-5 zeolite having a Si/Al atomic ratio ranging from 5 to 50. It is preferred that the incorporated triflic acid be in the range of 0.5 to 7% by weight. It is also preferred that the triflic acid incorporation be carried out by an uniform impregnation of triflic acid onto the ZSM-5 zeolite particles in the presence of an organic solvent, such as acetone. The resulting solid is heated at 80° C.—150° C. and preferably at 120° C.—140° C., for a period of time ranging from 1 hour to 24 hours.

Also within the scope of the present invention is a process for the conversion of dilute aqueous ethanol solutions to ethylene at temperatures ranging from 170° C. to 225° C., said process being characterized in that it comprises flowing a dilute aqueous ethanol solution through an acid form ZSM-5 zeolite having a Si/Al atomic ratio ranging from 5 to 50 and having incorporated therein 0.5 to 7% by weight of triflic acid. The preferred temperature range for the ethanol conversion is from 185° C. to 205° C.

Thus, in the context of the present invention, triflic acid is incorporated onto an acid form of as ZSM-5 zeolite. The high performance of the resulting catalyst in the conversion of aqueous ethanol into ethylene is due to the cooperative action of the zeolite acid sites and the triflic acid surface coating. It was found that triflic acid strongly reacted with the silica-alumina zeolite surface upon heating at 80°–150° C. The resulting bound triflic acid is stable at least up to 260° C. although pure triflic acid boils at 161° C. under atmospheric pressure. A similar stability is exhibited by sulfonic such as in Nafion ® resin (a perfluorinated resin sulfonic acid) and in Amberlyst 15 ® resin (macroreticular resin). Nafion ® resins were used as catalysts for the alkylation of isoparaffins, isomerization of normal alkanes, disproportionation of toluene, and the alkylation of benzene, at reaction temperatures up to 225° C. [J.D. McClure and S.G. Brandenberger, U.S. Pat. No. 4,060,565 (Nov. 29, 1977)].

Neither the acid form of the ZSM-5 zeolite alone or the triflic acid bearing silicalite (a silicalite is non acidic crystalline silicate having the ZSM-5 zeolite structure) as well as the triflic acid bearing Y-type zeolite and amorphorous gamma-alumina, exhibit comparable aqueous ethanol-to-ethylene catalytic activity and selectivity.

DETAILED DESCRIPTION AND PREFERRED EMBODIMENTS

The present invention relates to an acidic ZSM-5 zeolite coated with triflic acid, to a process for producing such a catalyst and to a process for the conversion of dilute ethanol solutions into ethylene at low temperatures using said catalyst.

The Zeolites

The zeolites which are directly concerned by the present invention belong to the family called ZSM or pentasil zeolite family namely ZSM-5 and ZSM-11 type zeolites.

The basic system can be a pure ZSM-5 zeolite under acid form (H-ZSM-5) or a composite ZSM-5 zeolite-asbestos material (also called ZSM-5 chryso-zeolite). The latter composite material is prepared by a multistep process which includes the partial leaching of the metallic components (magnesium and iron) from the chrysolite asbestos fibers, followed by the "in situ" zeolite crystallization and ended by the incorporation of the acid sites into the zeolite lattice. Preferably, H-ZSM-5 zeolites having a Si/Al atomic ratio in the range of 5 to 50 are used to prepare the catalyst of the present invention.

Trifluoromethanesulfonic Acid

In the context of the present invention, the trifluoromethanesulfonic acid (TFA) used can present a concentration varying from 10 to 100% but preferably a concentration of TFA higher than 98% is used.

Process For Preparing The TFA Coated HZM-5 Catalyst

The catalyst to be used in the context of the present invention is prepared by first intimately mixing a H-ZSM-5 zeolite having a Si/Al ratio ranging from 5 to 50 wherein the concentration of the incorporated triflic acid ranges from 0.5 to 75 by weight, with 5 to 50% by weight of an inert filler such as bentonite. Preferably, 20% by weight of an inert filler is used. The resulting mixture is made into a paste by adding a sufficient amount of distilled water. Although the amount of water incorporated may range from 0.5 to 3 ml for each gram of solid used, 1 ml of water for each gram of the solid represents the preferred portion. The resulting product is then dried and allowed to undergo surface reaction at a temperature ranging from 80° C. to 150° C. for a period of time ranging from 1 hour to 24 hours. The resulting sample is then ready to be used as a catalyst in the conversion of ethanol to ethylene.

Catalytic Conversion Of Ethanol To Ethylene

Conversion of ethanol in an aqueous solution having a concentration ranging from 2 to 15 weight % is usually defined by injecting the aqueous ethanol solution into a vaporizer-gas mixer. The vaporized solution may then be carried by an inert gas, for example nitrogen.

The flow rate of the carrier gas may range from 0 to 30 ml/mn. When an inert gas is not used to carry the vaporized solution, the latter may be carried by steam. The vaporized solution-carrier gas mixture is flown through a catalyst bed containing the catalyst in bead form having a density that can range between 0.5 and 1.5 cm$^3$. The temperature of the catalyst bed which is set in a tubular reactor contained inside a furnace may range between 170° C. and 225° C. The gaseous mixture flowing out of the reactor is then run through a series of condensers maintained at a temperature ranging between 5° and 10° C. to a liquid collector immersed is an ice bath followed by a cylinder from which gas sampling may be carried out. The resulting liquid and gaseous products are analyzed through gas or liquid chromotagraphy.

In the following examples, conversion to hydrocarbons is defined as the yield in hydrocarbons recovered during the run divided by the maximum theoretical yield in hydrocarbons according to the equation:

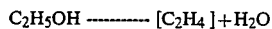

$$C_2H_5OH \longrightarrow [C_2H_4] + H_2O$$

product selectivity $S_i$ towards reaction product i is defined as follows:

$$S_i = Y_i/\Sigma Y$$

wherein $Y_i$ is the yield of the product i and $\Sigma Y$ is the yield of all the (hydrocarbon) products.

The following examples are listed to illustrate rather than limit the scope of the present invention.

EXAMPLE 1

Preparation of H-ZSM-5 (10)/TFA(2)

110 g of Baker silica gel dried at 120° C. for 12 hours, and having a silica content of 90 wt % were mixed with an aqueous solution containing 110 g of tetrapropylammonium bromide (Aldrich) and 7 g of NaOH dissolved in 300 ml of distilled water. The suspension was heated at 80° C. under vigorous stirring for one hour. Then a solution prepared from 22 g of sodium aluminate containing 46.79% wt of alumina and 28.44% by weight of sodium oxide dissolved in 90 ml of distiled water was added. Heating was continued at 80° C. with vigorous stirring for 10 minutes. The suspension was then transferred into a Parr autoclave lined with Teflon, and heated for 10 days at 170° C.±5° C. After cooling, the suspension was discharged from the autoclave and filtered, the solid was washed with distilled water until the washing liquid had a pH lower than 9 and was then dried at 120° C. for 12 hours and activated in the air at 550° C. for 12 hours.

The resulting solid was brought in contact with an aqueous solution of ammonium chloride (5% by weight), using 10 ml of solution per gram of compound. The suspension was heated at 80° C. under reflux with moderate stirring. After 1 hour of heating, the suspension was allowed to settle and the liquid was then rapidly removed.

A fresh volume of ammonium chloride solution was added and the suspension was again heated for another hour. The same procedure was repeated for several times so that the entire operation lasted 5 hours. The suspension was filtered and the solid was washed until Cl- ions were no longer present in the washing solution. The compound was dried at 120° C. for 12 hours and then activated in the air for 12 hours at 550° C.

The resulting acid-form of the ZSM-5 (10), called now H-ZSM-5 (10,powder), had the following chemical composition (% by weight): silica=90.8; alumina=9.1 and Na$_2$O=0.1 (Si/Al atomic ratio=10). Its degree of crystallinity was DC=94%, when determined according to the method of Le Van Mao et al (Canadian Journal of Chemistry 63, 3464 (1985)).

The incorporation of triflic acid onto the H-ZSM-5 (10) was done according to the following procedure: 0.2 g of triflic acid (TFA or trifluoromethanesulfonic acid, CF$_3$ SO$_3$H) 98% from Fluka Chemie AG were dissolved in 15 ml pure acetone. This solution was then slowly added to 10 g of H-ZSM-5 (10,powder) under moderate stirring. The resulting suspension was allowed to settle and dry in the air at room temperature. The obtained solid was then heated at 120° C. for 12 hours.

The final catalyst was prepared according to the following procedure: the previously obtained solid was intimately mixed with bentonite (20% by weight) and made into a paste with distilled water, 1 ml of water was used for each gram of the solid. Finally, the extrudates were dried at 120° C. for 12 hours. This sample was called H-ZSM-5 (10)/TFA (2).

EXAMPLE 2

Preparation of H-ZSM-5 (21)/TFA (2)

The same preparation procedure as previously described was used except for the initial gel composition used for the zeolite synthesis which comprised 110 g of silica gel Baker and 11 g of sodium aluminate Fischer. The resulting acid-form of the H-ZSM-5 (21, powder) had the following chemical composition (% by weight): silica=95.4; alumina=4.5 and Na$_2$O=0.1 (Si/Al atomic ratio=21). Its degree of crystallinity was 100%. The final catalyst was called H-ZSM-5 (21)/TFA (2).

EXAMPLE 3

Preparation of H-ZSM-5 (25)/TFA (3)

The same preparation procedure as described in Example 1 was used except for the initial gel composition used for the zeolite synthesis which comprised 110 g of silica gel Baker and 9.5 g of sodium aluminate Fischer. The resulting acid form of the H-ZSM-5 (25, powder) had the following chemical composition (% by weight): silica=96.5; alumina=3.5 and Na$_2$O=0.1 (Si/Al atomic ratio=25). Its degree of crystallinity was 100%.

The incorporation of triflic acid onto the H-ZSM-5 (25) was done according to the procedure described in Example 1 except for the weight of triflic acid used (0.3 g). The final catalyst was called H-ZSM-5 (25)/TFA (3).

EXAMPLE 4

Preparation of H-ZSM-5 (54)/TFA (2)

The same preparation procedure as described in Example 1 was used except for the initial gel composition used for the zeolite synthesis which comprised 110 g of silica gel Baker and 4.5 g of sodium aluminate Fischer. The resulting acid-form of the H=ZSM-5 (54,powder) had the following chemical composition (% by weight): silica=98.0; alumina=1.8 and Na$_2$O=0.2 (Si/Al atomic ratio=54). It degree of crystallinity was 99%. The final catalyst was called H-ZSM-5 (54)/TFA (2).

EXAMPLE 5

Preparation of H-ZSM-5 (10)

The previously obtained H-ZSM-5 (10,powder) (Example 1) was intimately mixed with bentonite (20% by weight) and made into a paste with distilled water, 1 ml of water was used for each gram of the solid. Finally, the extrudates were dried at 120° C. for 12 hours and activated in the air at 550° C. for 12 hours. This sample was called H-ZSM-5 (10).

EXAMPLE 6

Preparation of H-ZSM-5 (25)

The previously obtained H-ZSM-5 (25,powder) [Example 4] was intimately mixed with bentonite (20% by weight) and made into a paste with distilled water, 1 ml of water was used for each gram of the solid. Finally, the extrudates were dried at 120° C. by 12 hours and activated in the air at 550° C. for 12 hours. This sample was called H-ZSM-5 (25).

EXAMPLE 7

Preparation of Silicalite/TFA (2)

The silicalite, crystalline silicate having the ZSM-5 zeolite structure and used in this example was purchased from Union Carbide Molecular Sieves (powder, type S-115, >99% $SiO_2$). It was first dried at 120° C. for 12 hours and activated in the air at 550° C.

The incorporation of triflic acid onto the so-activated silicalite and the subsequent extrusion with bentonite were done using the procedure of Example 1. The resulting sample was called Silicalite/TFA (2).

EXAMPLE 8

Preparation o H-Y/TFA (2)

The $NH_4$-Y zeolite used in this example was purchased from Union Carbide Molecular Sieves (powder, type LZ-Y 82). According to the producer's technical information sheet, its chemical composition was (% by weight): silica=72.2; alumina=22.8; $Na_2O$=0,2 and $(NH_4)_2O$=4.0 (Si/Al atomic ratio=2.7). It was first dried at 120° C. for 12 hours and then activated in the air at 550° C. for 12 hours.

The incorporation of triflic acid onto the so-activated H-Y and the subsequent extrusion with bentonite were done using the procedure of Example 1. The resulting sample was called H-Y/TFA (2).

EXAMPLE 9

Preparation of Alumina (Ac)

The acidic aluminum oxide (powder) used in this example was purchased from Strem Chemicals Inc. (U.S.A.). It was first dried at 120° C. for 12 hours and then activated in the air at 550° C. for 12 hours. The extrusion with bentonite was done using the procedure of Example 1. The resulting sample was called Alumina (Ac).

EXAMPLE 10

Preparation of Alumina (92)/TFA (2)

The gamma-alumina (powder, >92 wt % in alumina, specific surface area=225 $m^2/g$) used in this example was purchased from Strem Chemicals Inc. (U.S.A.). It was first dried at 120° C. for 12 hours and then activated in the air at 550° C. for 12 hours. The incorporation of triflic acid onto the gamma-alumina and the subsequent extrusion with bentonite were done using the procedure of Example 1. The resulting sample was called Alumina (92)/TFA (2).

CATALYST TESTING

In order to evaluate the performance of the inventive catalysts, various runs, each using one of the above catalysts, were made. In each run the catalyst was used in bead form of density=0.50 $g/cm^3$.

Catalytic runs were performed by injecting an aqueous solution of ethanol having an ethanol concentration of 10% wt using an injection syringe on an infusion pump into a vaporizer-gas mixer. Nitrogen gas was supplied to the vaporizer-gas mixer at a flowrate of 20 ml/min. from a cylinder connected in series with a flowmeter. The vaporized feed was then carried by the nitrogen gas through a catalyst bed containing 4 g of catalyst set in a tubular reactor contained inside a furnace which was thermo-regulated at a temperature ranging from 170° to 205° C. A chromel-alumel thermocouple was placed in the catalyst bed and was used, in conjunction with a digital thermometer unit, to monitor the temperature of the catalyst bed. The gaseous mixture flowing out of the reactor was run through a series of condensers maintained at 5°-10° C., to a liquid collector immersed in an ice bath followed by a cylinder from which gas sampling was carried out.

Following a pre-run of 10 minutes, the liquid products were collected and the gaseous ones were analyzed periodically by gas chromatography (GC) using a 5 m long column packed with Chromosorb P ® coated with 20% by weight of Squalane ® connected in series with a 2.5 m long column packed with Carbopack ® graphite coated with picric acid (0.10 % by weight). The GC used was a dual F/D Hewlett-Packard Model 5790 equipped with a 3392 A model integrator. It was also equipped with a 50 m capillary column of the polymer which was used for accurate analyses of the liquid fractions after the completion of a run. The composition of the aqueous layer was also determined by GC (gas chromatograph) using a methanol in water calibration standard curve.

The other reaction conditions used in the experiments were as follows: total pressure=1 atm; weight hourly space velocity (W.H.S.V.)=0.9-4.5 $h^{-1}$; duration of a run=4 hours.

Table 1 reports the catalytic data obtained with the H-ZSM-5 (10)/TFA (2), the H-ZSM-5 (2) and the H-ZSM-5 (54)/TFA (2). The feed was aqueous solution of ethanol (10 wt %). The conversion to hydrocarbons was very high as well as the selectivity to ethylene when the reaction temperature ranged from 190° C. to 205° C. Some decrease in the conversion was observed with increasing W.H.S.V. (reaction temperature=205° C.). A reaction temperature lower than 180° C. led to lower conversion to hydrocarbons whereas the selectivity to ethylene was kept at very high levels.

It was observed that the H-ZSM-5 (10)/TFA (2) with a Si/Al atomic ratio=10 was more selective (towards ethylene) and more solactive than the H-ZSM-5 (21)/TFA (2) with a Si/Al atomic ratio=21. The difference in activity (conversion to hydrocarbons) is even larger with the H-ZSM-5 (54)/TFA (2) having a Si/Al atomic ratio of 54. In fact, this catalyst exhibited a 72.0% conversion at 200° C. while under the same reaction conditions. H-ZSM-5 (10)/TFA (2) and H-ZSM-5

(21)/TFA (2) gave 97.3% and 95.8% conversions respectively.

Moreover, similarly to data of Table 1, the conversion to hydrocarbons of the H-ZSM-5 (25)/TFA was ex-

TABLE 1

CATALYTIC DATA OF THE INVENTIVE CATALYSTS
(CONCENTRATION OF THE FEED AQUEOUS ETHANOL: 10 WT %)

| CATALYST | REACTION TEMPERAT. (°C.) | W.H.S.V. ($h^{-1}$) | CONVERSION to HYDROC. (%) | PRODUCT SELECTIVITIES (%) | | | |
|---|---|---|---|---|---|---|---|
| | | | | ETHYLENE | PROPYLENE | BUTENES | OTHER HYDROC. |
| H—ZSM-5 | 205 | 0.9 | 99.2 | 95.6 | 1.3 | 2.6 | 0.5 |
| (10)/ | 205 | 2.4 | 98.2 | 99.0 | 0.3 | 0.7 | — |
| TFA (2) | 205 | 4.5 | 90.0 | 99.7 | 0.1 | 0.2 | — |
| | 200 | 1.1 | 97.3 | 99.9 | 0.1 | — | — |
| | 190 | 0.9 | 94.8 | 99.1 | 0.3 | 0.5 | — |
| | 185 | 1.0 | 77.3 | 99.8 | 0.1 | 0.1 | — |
| | 180 | 1.1 | 73.9 | 99.2 | 0.3 | 0.4 | — |
| | 170 | 1.0 | 41.9 | 99.1 | 0.6 | 0.3 | — |
| H—ZSM-5 | 200 | 1.0 | 95.8 | 97.7 | 1.1 | 0.9 | 0.3 |
| (21)/ | 185 | 1.0 | 73.7 | 99.3 | 0.3 | 0.3 | 0.1 |
| TFA (2) | | | | | | | |
| H—ZSM-5 (54)/TFA (2) | 200 | 1.0 | 72.0 | 98.1 | 0.4 | 1.5 | — |

TEMPERAT. = temperature
HYDROC. = hydrocarbons

Table 2 reports the catalytic data obtained with comparative samples. Acidic (amorphous) aluminium oxide [Alumina (Ac) sample] and acidic (crystalline aluminosilicate) ZSM-5 zeolite [H-ZSM-5 (10) sample] did not exhibit any significant catalytic activity at 200° C. The triflic acid incorporated onto inert matrices [but having high surface area such as the amorphous alumina (92) and the crystalline/non acidic silicalite with the ZSM-5 zeolite structure] also did not give any significant catalytic activity at this temperature.

The triflic acid incorporated onto acidic Y-zeolite matrix [H-Y/TFA (2) sample] yielded more ethylene than other comparative catalysts of Table 2. However, its conversion to hydrocarbons (43.4%) was much lower than that of the catalysts [H-ZSM-5 (10)/TFA (2) and H-ZSM-5 (21/TFA (2)] of the present invention tested under the same reaction conditions (conversion : 97.3% and 95.8%, respectively).

tremely high when compared to that of the H-ZSM-5 (25) (see Table 3).

Since triflic acid has a boiling point of 161° C. (under atmospheric pressure), the thermal stability of the triflic acid coated on the zeolite surface is due to the reaction between the surface silicon and probably also aluminum atoms of the zeolite and the triflic acid during the heating of the catalyst at 80° C. −150° C. This chemical linkage of triflic acid to the zeolite surface is similar to the "chemical anchorage" of the triflic acid to an organic polymer such as in the Nafion ® resin [see U.S. Pat. No. 4,060,565 (Nov. 29, 1977)].

The second advantage found with the "H-ZSM-5/triflic acid" system is that the ZSM-5 zeolite framework has a pore size of circa 5.5 angstroms: this contributes to enhancing the selectivity to ethylene and decreasing the formation of bulky molecules (see Table 1). The "H-Y/triflic acid" exhibited a non-negligible conversion to

TABLE 2

CATALYTIC DATA OF THE COMPARATIVE CATALYSTS
Reaction conditions: temperature: 200° C., W.H.S.V.: 1.0 $h^{-1}$,
ethanol concentration in water: 10 wt %.

| CATALYST | CONVERSION TO HYDROCARBONS (%) | PRODUCT SELECTIVITIES (%) | | | |
|---|---|---|---|---|---|
| | | ETHYLENE | PROPYLENE | BUTENES | OTHER HYDROC. |
| H—ZSM-5 (10) | 14.0 | 99.8 | 0.2 | — | — |
| Alumina (Ac) | 0.0 | — | — | — | — |
| Alumina (92).TFA (2) | 0.0 | — | — | — | — |
| Silicalite/TFA (2) | 13.7 | 99.6 | 0.3 | 0.1 | — |
| H-Y/TFA (2) | 43.4 | 93.8 | 1.9 | 3.4 | 0.9 |

HYDROC. = hydrocarbons

Table 3 reports the catalytic data obtained with the H-ZSM-5 (25) catalyst as well as those of the inventive catalyst, the H-ZSM-5 (25)/TFA (3). The latter had been activated at nitrogen atmosphere at 260° C. and 200° C. respectively, for 3 hours prior to the reaction at 180° C. No significant change was observed when the temperature of treatment was 260° C. instead of 200° C.: this means that the catalyst was stable up to 260° C.

hydrocarbons (see Table 2). However, due to larger pore size (10 angstroms), the H-Y favors the formation of some high weight compounds which by decomposition over superacidic sites generate carbonaceous species. Thus, "H-Y/triflic acid" sample undergoes a much more rapid decay in activity than the "H-ZSM-5/triflic acid" catalysts.

TABLE 3

Catalytic data of the inventive catalyst H—ZSM-5 (25)/TFA (3) treated at two different temperatures, and those of the comparative catalyst H—ZSM-5 (25). (reaction conditions: W.H.S.V.; 1.0 h$^{-1}$; ethanol concentration in water: 10 wt % and temperature: 180° C.)

| CATALYST | TEMPERATURE OF TREATMENT (°C.) | CONVERSION TO HYDROCARBONS (%) | PRODUCT SELECTIVITIES (%) | | | |
|---|---|---|---|---|---|---|
| | | | ETHYLENE | PROPYLENE | BUTENES | OTHER HYDROC. |
| H—ZSM-5 (25) | 550 | 5.6 | 99.5 | 0.3 | 0.2 | — |
| H—ZSM-5 (25)/TFA (3) | 200 | 53.1 | 99.6 | 0.3 | 0.1 | — |
| H—ZSM-5 (25)/TFA (3) | 260 | 56.4 | 99.9 | 0.1 | — | — |

HYDROC. = hydrocarbons

In view of the results obtained, the following aspects may be pointed out:

(a) H-ZSM-5 zeolite and triflic acid are both acid catalysts. H-ZSM-5 can dehydrate aqueous ethanol to ethylene at temperatures ranging from 275° C. to 350° C. However, at 200° C., its activity is very low. Triflic acid incorporated onto non-acidic matrices [gamma-alumina (92) or silicalite] does not exhibit any noticeable ethanol dehydrating activity. It is to be noted that triflic acid normally boils at 161° C.

The exceptional ethanol dehydrating performance of the H-ZSM-5 (10)/TFA (2) is due to the cooperative action between two active conters, namely the zeolitic and sulfonic acid sites which are chemically linked to the zeolite surface. The Si/Al atomic ratio of the H-ZSM-5 zeolite influences to a small but noticeable extent the selectivity of the overall catalyst. In other words, the lower the Si/Al atomic ratio, the better the selectivity of the final catalyst towards ethanol conversion into ethylene.

(b) The triflic acid incorporated onto a H-Y zeolite shows an interesting conversion at 200° C.; however, this catalytic performance is much lower than that of the triflic acid bearing ZSM-5 zeolite.

Since H-Y zeolite is richer in aluminium sites than the H-ZSM-5 (10), the acid density i.e. that of the number of acid sites by weight unit of the H-Y is much higher than the H-ZSM-5 (10). However, the H-ZSM-5 zeolites are known to have stronger acid sites than other Al richer zeolites such as the H-Y zeolite. Thus, acidity strength seems to be an important factor of the catalytic conversion of ethanol to ethylene.

Another advantage of the TFA coated ZSM-5 zeolite stands on the pore diameter which is circa 5 angstroms. The bulkiest molecule which can be adsorbed by the modified ZSM-5 zeolite is benzene. Thus, no oligomeric species is formed within the H-ZSM-5/TFA pore system and this contributes to keep the superacidic sites clean from any carbonaceous deposit for a long period of time. Moreover, bulky molecules such as lignin derivatives obtained from biomass treatment process for the recovery of cellulose and hemicellulose and yeast residues and not completely removed from the ethanol fermentation broth are prevented from entering the catalyst pores.

Thus, there will not be any decomposition of these compounds onto the active sites of the catalyst which are mainly located within the zeolite pores and no catalyst activity decay will be due to such decomposition reactions.

We claim:

1. A catalyst comprising from 0.5 to 7% by weight of trifluoromethanesulfonic acid incorporated onto an acid-form pentasil zeolite having a Si/Al atomic ratio ranging from 5 to 50.

2. The catalyst of claim 1, wherein the incorporated trifluoromethanesulfonic acid is allowed to react with the silicon rich surface of the zeolite at a temperature ranging from 80° C. to 150° C.

3. The catalyst of claim 1, which further comprises an inert binder.

4. The catalyst of claim 2, wherein said binder is bentonite.

5. A process for preparing the catalyst of claim 1, which comprises reacting at a temperature of from 80 to 150° C. for a period of time of from 1 to 24 hours trifluoromethanesulfonic acid with the silicon rich surface of an acid-form pentasil zeolite having a Si/Al atomic ratio of from 5 to 50.

6. The process of claim 5, wherein the product obtaineds activated in an inert medium at a temperature of from 180° C. to 275° C. for a period of from 1 to 12 hours.

* * * * *